(12) United States Patent
Vallespi et al.

(10) Patent No.: US 8,283,324 B2
(45) Date of Patent: Oct. 9, 2012

(54) IMMUNOMODULATORY AND ANTI-TUMOUR PEPTIDES

(75) Inventors: Maribel Guerra Vallespi, Ciudad de La Habana (CU); Isis del Carmen Torréns Madrazo, Ciudad de La Habana (CU); Osvaldo Reyes Acosta, Ciudad de La Habana (CU); Hilda Elisa Garay Pérez, Ciudad de La Habana (CU); Gerardo Enrique Guillén Nieto, Ciudad de La Habana (CU); Boris Ernesto Acevedo Castro, Ciudad de La Habana (CU); Raimundo Ubieta Gómez, Ciudad de La Habana (CU)

(73) Assignee: Centro de Ingenieria Genetica y Biotecnologia (CU)

( * ) Notice: Subject to any disclaimer, the term of this patent is extended or adjusted under 35 U.S.C. 154(b) by 0 days.

(21) Appl. No.: 12/278,990

(22) PCT Filed: Feb. 23, 2007

(86) PCT No.: PCT/CU2007/000006
§ 371 (c)(1),
(2), (4) Date: Dec. 31, 2008

(87) PCT Pub. No.: WO2007/095867
PCT Pub. Date: Aug. 30, 2007

(65) Prior Publication Data
US 2009/0221508 A1    Sep. 3, 2009

(30) Foreign Application Priority Data

Feb. 24, 2006    (CU) .......................................... 47/06

(51) Int. Cl.
*A61K 38/16*    (2006.01)
*C07K 14/00*    (2006.01)

(52) U.S. Cl. ..................................... 514/21.4; 530/326

(58) Field of Classification Search .................. None
See application file for complete search history.

(56) References Cited

U.S. PATENT DOCUMENTS 6,384,188 B1 * 5/2002 Hoess et al. .................. 530/326
6,632,793 B1 * 10/2003 Vallespi et al. ................. 514/13

OTHER PUBLICATIONS

Vallespi et al., Journal of Peptide Science, 16:40-47, 2010.*
Reyes et al., Journal of Peptide Science, 8:144-150, 2002.*
Lamping et al., Journal of Immunology, 157:4648-4656, 1996.*

* cited by examiner

*Primary Examiner* — Marianne P Allen
(74) *Attorney, Agent, or Firm* — Hoffmann & Baron, LLP

(57) ABSTRACT

The present invention is related to the development of peptides derived from the sequence HYRIKPTFRRLK-WKYKGKFW (SEQ ID NO.: 13), showing amino acid substitutions, these peptides unable to bind to the lipopolysaccharides and bearing anti-tumoral and immunomodulatory capacities. These peptides alone or in combination are useful to treat cancer, and also in synergy with conventional therapies.

18 Claims, 8 Drawing Sheets

IMMUNOMODULATORY AND ANTI-TUMOUR PEPTIDES

This application is the U.S. National Phase of, and Applicants claim priority from, International Application Number PCT/CU2007/000006 filed 23 Feb. 2007 and Cuban Application bearing Serial No. CU 2006-0047 filed 24 Feb. 2006, which are incorporated herein by reference.

FIELD OF TECHNIQUE

The present invention is included in the field of cancer immunotherapy. More precisely, peptides derived from the sequence 32-51 of the *Limulus* anti-LPS factor protein or their combinations, unable to bind to lipopolysaccharides and useful for treating cancer and metastasis.

BACKGROUND

The use of modifiers of the biological response for treating cancer mainly combined with current therapies to enhance the benefit of treatment has been recently reported (US 2004/0101511). On the other hand, the use of CpG sequences, the agonist of the Toll-like receptor 9 (TLR9), has been developed as new drugs for treating, controlling and preventing cancer as parts of multiple treatment indications, i.e. non-small cells lung cancer, melanoma and renal carcinoma (Klinman D. M., et al, (2004) Immunotherapeutic uses of CpG oligodeoxynucleotides. *Nat Rev Immunol.* 4:249-258). A Toll-like receptor 7 (TLR7) agonist is currently tested in phase I clinical trials for activating the immune system, with promising results as a new drug for treating melanoma and other tumors (Dudek A. Z., et al (2005) ASCO Annual Meeting). The previously mentioned agonists of TLRs 7 and 9 are also being evaluated in viral infections, based on their capacity to promote an effective immune response in the host. Besides, the named Heat shock proteins (Hsp) that bind to the TLR4, have been developed and manufactured as a fusion protein to the human papillomavirus (HPV) E7 oncoprotein. This new immunotherapeutic approach is also known as therapeutic vaccines, with (Chu N. R. et al., (2000) Immunotherapy of a human papillomavirus (HPV) type 16 E7-expressing tumour by administration of fusion protein comprising *Mycobacterium bovis* bacille Calmette-Guerin (BCG) hsp65 and HPV16 E7. *Clin Exp Immunol* 121:216-225). a wide perspective for treating human papillomavirus-related diseases. Toll-like receptors are receptor molecules present in cells of the immune system, recognizing pathogen-associated molecular patterns, like LPS, lipoteichoic acid, unmethylated CpG sequences and viral double- and single-stranded RNA. The recognition of the invading pathogen by TLRs helps the immune system to direct a balanced Th1/Th2 immune response to efficiently eradicate the infection out of the organism. The use of TLRs agonists as drugs to treat cancer is based on the activating the innate and adaptive immune systems, by activating a Th1 immune response mediated by type I interferons (e.g. α & β IFNs) and interleukin 12 (IL-12) as the main mechanism. Therefore, a highly specific and sustained immune response is achieved (Switaj T., Jalili A., et al., (2004) CpG Immunostimulatory oligodeoxynucleotide 1826 enhances antitumor effect of interleukin 12 gene-modified tumor vaccine in a melanoma model in mice. *Clinical Cancer Research, Vol.* 10:4165-4175). This dual activation of the immune system contrasts with several other immunotherapeutic approaches which are unable to generate a sustained effect in the adaptive immune response and also unspecifically activating the innate immune system with subsequent undesired effects (Speiser D. E, et al. (2005) Rapid and strong human CD8+ T cell responses to vaccination with peptide, IFA, and CpG oligodeoxynucleotide 7909. *The Journal of Clinical Invest. Vol.* 115 (3)).

Dendritic cells (DCs) are professional antigen presenting cells linking innate and adaptive immune responses through cell-to-cell interactions and cytokine production. DCs are classified in myeloid or lymphoid attending to their origin, based on differential expression of a series of surface molecular markers and also TLRs. Lymphoid DCs, also known as plasmacytoid DCs, are the main source of type I interferons. Considering these properties, DCs have been manipulated as promising cellular adjuvants to develop therapeutic vaccines against cancer and chronic viral infections (Santini S. M., et al (2003) A new type I IFN-mediated pathway for rapid differentiation of monocytes into highly active dendritic cells. *Stem Cells,* 21:357-362). However, this is a very expensive and difficult technique, with other more practical and less expensive therapeutic strategies under development (Van Epps H. L. (2005) New hope for tumor vaccines. *The Journal of Experimental Medicine*, Vol. 202:1615).

Originally described by their antiviral activity, type I interferons (α,β IFNs) have been recently shown to exert important effects over the immune system, promoting cellular and humoral immune responses through their adjuvant effects on DCs (Bogdan, C. (2000) The function of type I interferons in antimicrobial immunity. *Curr, Opin Immunol.* 12:419-424). Recent works have shed lights on the critical role of endogenous type I interferons in processes mediating regression of a highly immunogenic syngenic murine sarcoma, and protecting the host against the occurrence of primary carcinogenic tumor (Gavin P. Dunn, et al. (2005) A critical function for type I interferons in cancer immunoediting. *Nature Immunology, June* 12). Resides, IFN-α plays an important role in initiating the antiviral T-lymphocyte response through direct activation of CD4+ or CD8+ T lymphocytes in viral infections like Influenza (Fonteneau J. F, et al. (2003) Activation of influenza virus-specific $CD^+4$ and $CD^+8$ T cells: a new role for plasmacytoid dendritic cells in adaptive immunity. *Immunobiology,* 101: 3520-3526).

Hoess (WO 95/05393) relates in his invention substances binding LPS with high affinity, useful for preventing or treating infections like gram-positive or gram-negative bacteria-mediated sepsis, bacterial infections in general and fungal infections. Such substances are LPS-binding peptides bearing an endotoxin-binding domain (Hoess A., et al, (1993) Crystal structure of an endotoxin-neutralizing protein from the horseshoe crab, *Limulus* anti-LPS factor, at 1.5 A° resolution. The *EMBO J.* 12:3351-3356). The crystal structure of the original *Limulus* anti-LPS factor (LALF) protein reveals a loop similar to polymyxin B, positively charged, amphipathic and containing exposed hydrophobic and aromatic residues. Based on this principle, he documented the capacity of sequences corresponding to aminoacids 31 to 52 on the LALF protein to bind and neutralize the effects associated to heparin, like anti-coagulation, angiogenesis and inhibition of endothelial and tumor cells' proliferation. However, there are no experimental data supporting this statement in the patent mentioned above. In fact, claims granted referred to a device for removing LPS in solution, wherein said device comprises peptides immobilized in a solid support (U.S. Pat. No. 6,384, 188).

On the other hand, Vallespi (U.S. Pat. No. 6,191,114) relates in her invention the antiviral effect of the $LALF_{31-52}$ peptide on Hep-2 and MDBK cells, mediated by the production of α and γ interferons, also relating her invention to the use of this peptide for treating viral infections and immunosuppression-related disorders. Moreover, the same author has demonstrated the anti-infection effect of this peptide in animal models of sepsis (Vallespi M. G., et all (2003) *A Limulus anti-LPS factor-derived peptide modulates cytokine gene expression and promotes resolution of bacterial acute infection in mice. International Immunopharmacology,* 3:247-256).

There are a number of therapies directed against cancer, including chemotherapy, radiations and gene therapy. Toxicity is one major disadvantage of all these therapies, with high doses been administered for prolonged periods of time to finally achieve some beneficial therapeutic effect. Therefore, there is still required the development of new drugs for gaining more effective treatments.

Based on the essential role of the immune system to detect and direct an efficient response against tumors, drugs designed to activate the host innate and adaptative defense mechanisms can become powerful tools for cancer therapeutics.

There are no previous amino acid substitutions described for the sequence HYRIKPTFRRLKWKYKGKFW (SEQ ID NO: 13) of the LALF protein, eliminating its LPS-binding capacity and enhancing the immunomodulatory effect, also conferring anti-tumoral effects in vivo against several tumors.

DETAILED DESCRIPTION OF THE INVENTION

The present invention solves problems previously mentioned, providing peptides derived from the 32-51 region of the LALF protein sequence HYRIKPTFRRLK-WKYKGKFW (SEQ. ID. NO: 13), wherein amino acids have been substituted to eradicate the LPS-binding capacity and enhance the ant-tumoral and immunomodulatory effect.

Analogous peptides, derived from said sequence by substitutions forbidding LPS— or heparin-binding and also providing increased anti-tumoral and immunomodulatory effects compared to the original peptide, consist on the following sequences:

| HARIKPTFRRLKWKYKGKFW | (SEQ. ID. NO: 1) |
| HYRIKPTARRLKWKYKGKFW | (SEQ. ID. NO: 2) |
| HYRIKPTFRRLAWKYKGKFW | (SEQ. ID. NO: 3) |
| HYRIKPTFRRLKWKYKGKFA | (SEQ. ID. NO: 4) |

The LPS-binding peptides described by Hoess and Vallespi are disadvantageous in that they deviate a mixed Th1/Th2 profile toward a predominant Th2 profile, detrimental for cancer patients. These patients commonly present concomitant infections due to immunodepression, not ruling out the presence of LPS particles in blood. The administration of a peptide inducing a predominant Th2 profile in the presence of LPS would result in undesired effects, further deteriorating the patient's immunological status and worsening the host response against the tumor. Moreover, the binding to LPS of the peptide described by Vallespi would minimize the immunomodulatory effect of this peptide.

On the other hand, the lack of binding to heparin of peptides described in the present invention make them superior to those previously described by Hoess and Vallespi. In critical patients like those suffering from ischemic cardiopathy, cerebrovascular disease, venous thromboembolic disease (deep vein thrombosis and pulmonary embolism) and hind limb ischemia, heparin is indicated as treatment (D. Cabestrero Alonso, et al (2001) Heparinas de bajo peso molecular en pacientes criticos: usos, indicaciones y tipos. *Medicina Intensiva,* Vol. 95:18-26). Subsequently, by administering a heparin-binding peptide could be contraindicated in this context, because of interfering with the effect of this drug. The association of cancer and thromboembolic diseases is a well described phenomenon that can significantly contribute to morbidity and mortality in cancer patients, like deep venous thrombosis and pulmonary embolism. Based on these reasons previously mentioned, the availability of peptides unable to bind heparin and showing an anti-tumoral and immunomodulatory effect in the treatment of cancer patients is advantageous, a significant percent of these patients commonly subjected to surgery and presenting other disorders like hypercoagulation (Castelli R., et al (2004) The heparins and cancer: Review of clinical trials and biological properties. *Vascular Medicine,* Vol. 9:1-9).

The invention also includes peptides with two or more aminoacids substituted by alanine, comprising the following aminoacid sequences:

| HYRIKPTARRLAWKYKGKFW | (SEQ. ID. NO: 8) |
| HARIKPTARRLKWKYKGKFW | (SEQ. ID. NO: 9) |
| HARIKPTFRRLAWKYKGKFW | (SEQ. ID. NO: 10) |
| HARIKPTARRLAWKYKGKFW | (SEQ. ID. NO: 11) |
| HARIKPTARRLAWKYKGKFA | (SEQ. ID. NO: 12) | and any other homologous or mimetic variant of these previous peptides, obtained by synthetic or recombinant procedures, and as part of any fusion peptide. The homologous variant is referred as any peptide devoid of LPS- or heparin-binding capacity and bearing an anti-tumoral and immunomodulatory effect. Similarly, the said mimetic variant is referred as any molecule of chemical origin (non-protein) which structure is devoid of LPS- or heparin-binding capacity and maintaining a anti-tumoral and immunomodulatory effect.

In a preferred embodiment of the present invention, the pharmaceutical composition contains one or more peptides and chemical compounds or their respective pharmaceutically acceptable salts, as well as pharmaceutically acceptable excipients or vehicles.

In other preferred embodiment of the present invention, the pharmaceutical composition additionally contains an antigen selected from the group comprising a bacterial, viral or cancer antigen.

Similarly, the peptides of the present invention could be used in combination with conventional treatments against cancer, like chemotherapy, surgery, radiation, etc. The present invention also comprises the use of these peptides and chemical compounds for preparing a pharmaceutical composition for treating and/or preventing immunological disorders requiring an effective Th1 immune response; treatment or prevention of cancer and to develop an effective immune response against infections of bacterial or viral origin.

The peptides described were defined by being devoid of LPS-binding capacity, instead of the original HYRIKPTFR-RLKWKYKGKFW (SEQ ID NO: 13) sequence, previously described as an consensus optimal domain for LPS binding (Hoess et al., (1993). Crystal structure of an endotoxin-neutralizing protein from the horseshoe crab, Limulus anti-LPS factor, at 1.5 A° resolution. (*The EMBO J.* 12:3351-3356). In the same way, the peptides described in the present invention enhance the immunomodulatory effect, mediated by secretion of IFN-α, compared to the peptide derived from the LALF protein that comprises amino acids 31 to 51 that Vallespi refers in her patent (U.S. Pat. No. 6,191,114) as an antiviral and immunomodulatory peptide.

Similarly, the peptides described in the invention can be administered to immunosuppressed patients and those requiring an activation of their immune status, like patients suffering from the acquired immunodeficiency syndrome (AIDS) and patients subjected to complex surgery.

Experimental in vivo data demonstrated the effectiveness of analogous peptides in tumors implanted in mice, these tumors derived from murine melanoma B16 cells; malignant lung epithelial cells from C57Bl/6 mice and 3LL-D122 cells obtained from mice lung cancer.

In another embodiment, peptides can be administered to minimize metastatic events.

Other results of the present invention indicate that the peptides described show anti-proliferative effects on tumor cell lines of varied histological origin, demonstrating a direct cytotoxic effect over cancer cells.

In principle, the peptides described can be used alone or combined with current therapies for treating cancer, like surgery, radiation or chemotherapy.

Similarly, the peptides described in the present invention when administered prophylactically generate a rapid innate immune response against the tumor, subsequently developing an adaptive antigen-specific immune response, emphasizing their use in prophylactic or therapeutic vaccines against cancer.

BRIEF DESCRIPTION OF FIGURES

FIG. 1: Effect of peptides over the bacterial lipopolysaccharide (LPS)-binding capacity.

EXAMPLES

Example 1

Peptide Synthesis

The peptides of the invention are synthesized following a solid phase procedure. The crude peptide is extracted with a 30% acetic acid solution, lyophilized and further purified by RP-HPLC. The molecular weights of purified peptides are checked by using a mass spectrometer JEOL JMS-HX110HF with a FAB gun. The resulting preparation is non-antigenic, non-pyrogenic and pharmaceutically acceptable for administering in animals and humans. Substitutions were carried out by introducing the alanine aminoacid into each position of the original sequence of the peptide HYRIKPTFRRLK-WKYKGKFW (SEQ ID NO.: 13).

Example 2

Selecting Analogous Peptides Devoid of Lipopolysaccharide (LPS)-Binding Capacity This assay consists on a competition ELISA system (Hardy E., et al (1994) Enhanced ELISA sensitivity using TCA for efficient coating of biologically active LPS or Lipid A to the solid phase. *J. Immunol. Meth. Vol.* 176:111-116). Polystyrene plates (Costar, USA) were coated with LPS from *E. coli* 0111:B4 (1 µg/ml) with 0.2% trichloroacetic acid (TCA). Plates were incubated overnight at 37° C. and further washed ten times with 1× phosphate-buffered saline (1×PBS) plus 0.1% tween-20 (washing solution). The binding of analogous peptides to the LPS fixed to the solid surface was evaluated by a competition ELISA with the biotinylated $LALF_{32-51}$ peptide at 0.2 µM, obtaining a 90% of maximum LPS binding. To estimate the inhibition curves, different concentrations of the analogous peptides were used, from 10 µM to 0.01 µM and the curve of the $LALF_{32-51}$ peptide as experimental control. The biotinylated $LALF_{32-51}$ was incubated in the presence of the analogous peptides for 2 h at 37° C. and plates were washed 5 times after that time with washing solution. The biotinylated $LALF_{32-51}$ bound to LPS was detected by incubating for 45 min at 37° C. with a streptavidin-peroxidase conjugate at a 1:2,000 dilution. Plates were washed 5 times with washing solution and the substrate solution was added (0.05 M citrate-phosphate buffer, pH 5.5, 1 tablet of 3,3',5,5'-tetramethylbenzidine and 0.025% hydrogen peroxide). After 15 min incubation, the reaction was stopped by adding 2 M sulphuric acid. The absorbance was quantified at 450 nm in a plate reader (Sensident Scan). There is a correlation between optical density values and the LPS-binding capacity of analogous peptides. Analogous peptides with higher LPS-binding capacity show inhibition curves of lower O.D. compared to the inhibition curve of the $LALF_{32-51}$ peptide.

Figure 1A:
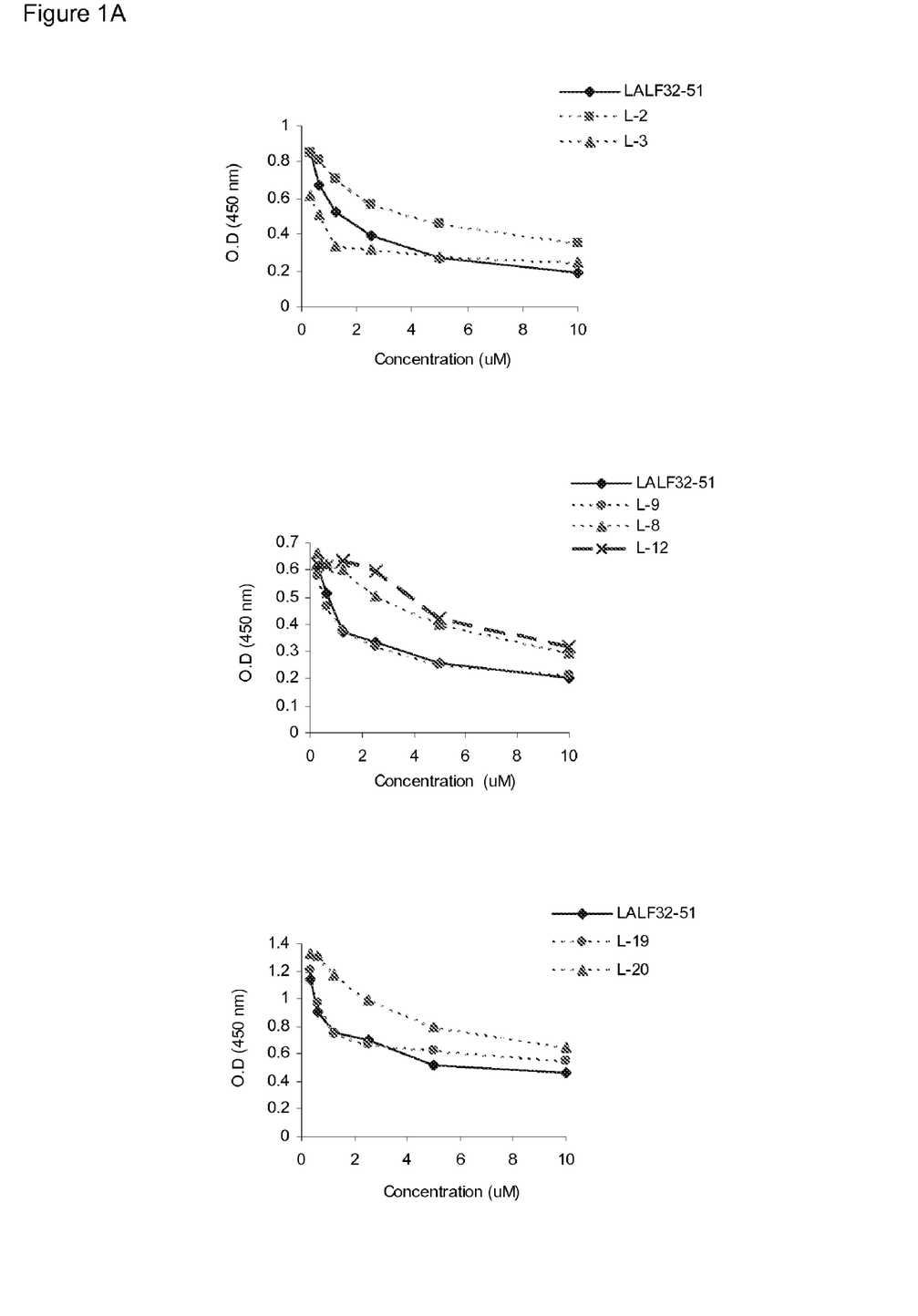
FIG. 1A, these experiments were conducted by triplicate; inhibition curves of one experiment are shown. Percentages of inhibition shown in FIG. 1B represent the mean of three independent experiments.

Analogous peptides with lower LPS-binding capacity present inhibition curves with O.D. values, compared to the inhibition curve of the $LALF_{32-51}$ peptide. Results are shown in FIG. 1A, demonstrating that peptides named L-2, L-8, L-12 and L-20 lose the capacity to bind LPS, with peptides L-9 and L-19 retaining that capacity, similar to the $LALF_{32-51}$ peptide. On the other hand, L-3 peptide shows a higher LPS binding capacity.

Figure 1B:
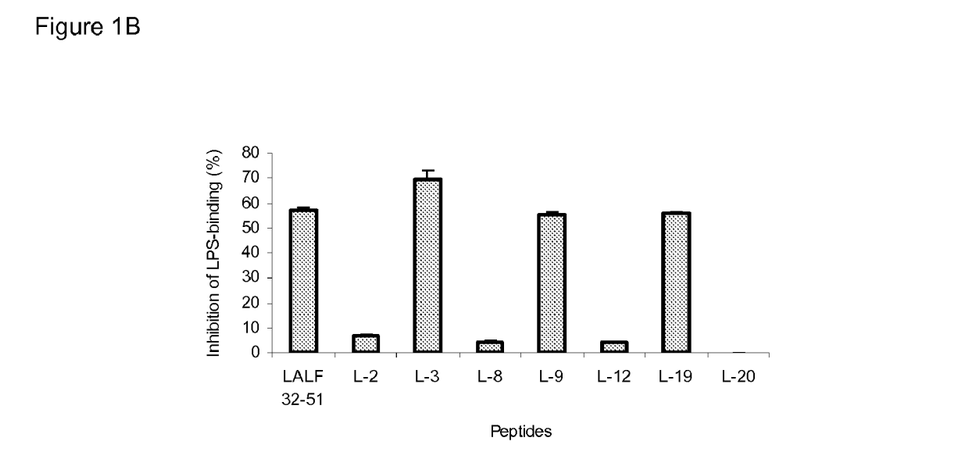

FIG. 1B represents the inhibition percentages of analogous peptides, at a fixed 0.5 M concentration, according to their capacity to displace the binding of the biotinylated $LALF_{32-51}$ (0.2 µM) to LPS adsorbed to the solid surface.

% de inhibición=$\{1-(([O.D.]_{sample}-[O.D.]_{min})/([O.D.]_{max}-[O.D.]_{min}))\} \times 100$

[O.D.] sample: Optical density value in the presence of a fixed concentration of analogous peptides;
[O.D.] min: ELISA background;
[O.D.] max: Optical density value without analogous peptides.

Table 1. Sequence of peptides used in the examples

| Peptide | Aminoacid sequence | | |
|---------|---------|---|---|
| L-2  | $_{32}$HARIKPTFRRLKWKYKGKFW$_{51}$ | (SEQ. ID. NO: 1) | |
| L-3  | $_{32}$HYAIKPTFRRLKWKYKGKFW$_{51}$ | (SEQ. ID. NO: 5) | |
| L-8  | $_{32}$HYRIKPTARRLKWKYKGKFW$_{51}$ | (SEQ. ID. NO: 2) | |
| L-9  | $_{32}$HYRIKPTFARLKWKYKGKFW$_{51}$ | (SEQ. ID. NO: 6) | |
| L-12 | $_{32}$HYRIKPTFRRLAWKYKGKFW$_{51}$ | (SEQ. ID. NO: 3) | |
| L-19 | $_{32}$HYRIKPTFRRLKWKYKGKAW$_{51}$ | (SEQ. ID. NO: 7) | |
| L-20 | $_{32}$HYRIKPTFRRLKWKYKGKFA$_{51}$ | (SEQ. ID. NO: 4) | |

As results from these analyses, double, triple and quadruple mutations were carried out, starting from peptides devoid of LPS-binding capacity:

| | | |
|---|---|---|
| HYRIKPTARRLAWKYKGKFW | (SEQ. ID. NO: 8) | |
| HARIKPTARRLKWKYKGKFW | (SEQ. ID. NO: 9) | |
| HARIKPTFRRLAWKYKGKFW | (SEQ. ID. NO: 10) | |
| HARIKPTARRLAWKYKGKFW | (SEQ. ID. NO: 11) | |
| HARIKPTARRLAWKYKGKFA | (SEQ. ID. NO: 12) | |

Example 3

Evaluation of Heparin-Binding Capacity of Analogous Peptides L-2, L-8, L-12 and L-20

Figure 2:
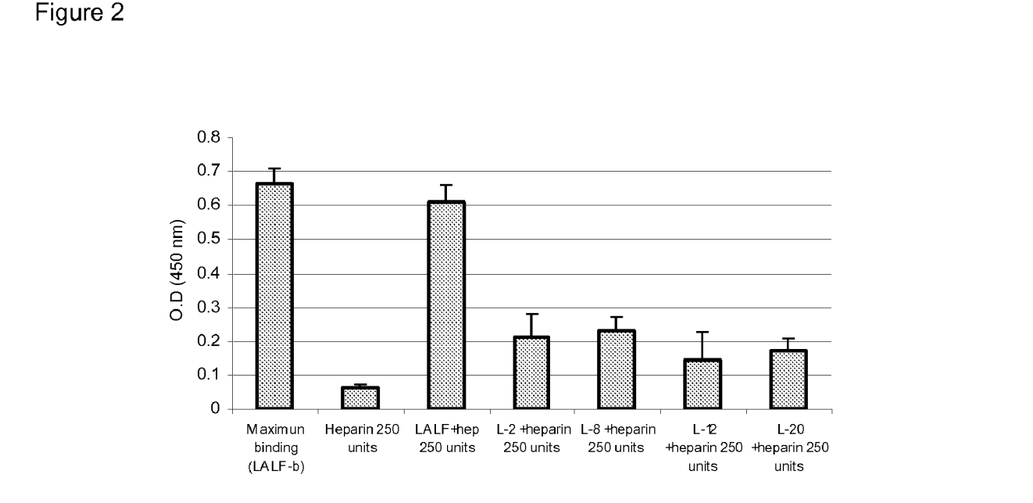
FIG. 2: Effects of peptides on the capacity to bind the anionic compound heparin. The mean of three independent experiments is shown.

This assay consists on a competition ELISA system, similar to the previously described one. The biotinylated LALF$_{32-51}$ peptide was adsorbed to polystyrene plates (Costar, USA) in 1×PBS and incubated overnight at 4° C. Analogous peptides L-2, L-8, L-12 and L-20 were mixed at 2 μM with 250 units of heparin (Sodic Heparin, 5,000 U/ml, Liorad) in 1×PBS plus 0.1% of bovine serum albumin (BSA). Afterwards, mixes were added to an ELISA plate containing 0.02 μM of the biotinylated LALF$_{32-51}$ peptide adsorbed to the solid surface. After a 1 h-incubation at room temperature, plates were washed five times with washing solution and the biotinylated LALF$_{32-51}$ peptide fixed to the solid surface was detected by incubating for 45 min at 37° C. with streptavidin-peroxidase conjugate at a 1:2,000. Afterwards, plates were washed five times with washing solution and the substrate solution was added. After an additional incubation for 15 min, the reactions were stopped with 2 M sulphuric acid solution. The lack of heparin binding to the analogous peptides correlates with the decreased optical density, because they are unable to displace the heparin bound to the biotinylated LALF$_{32-51}$ peptide adsorb to the solid surface. The unlabeled LALF$_{32-51}$ peptide at a 100× molar excess was used as control of the assay. The binding to heparin of the unlabeled LALF$_{32-51}$ peptide is demonstrated by the increased optical density values, because the excess of cold peptide competes by the binding to heparin. As shown in FIG. 2, results indicate that peptide L-2, L-8, L-12 and L-20 described in the present invention are unable to bind heparin.

Example 4

Figure 3A:
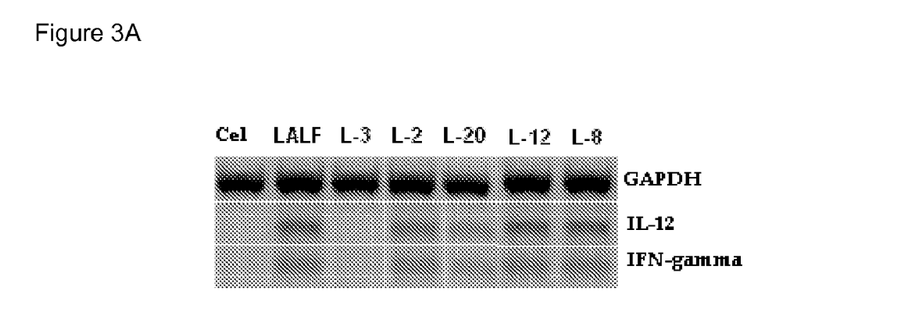
FIGS. 3a and 3b: Effects of peptides on the production of a and y interferons and IL-12 in human mononuclear cells. Three experiments were conducted with different donors, shown the results of one of them.
Figure 3B:
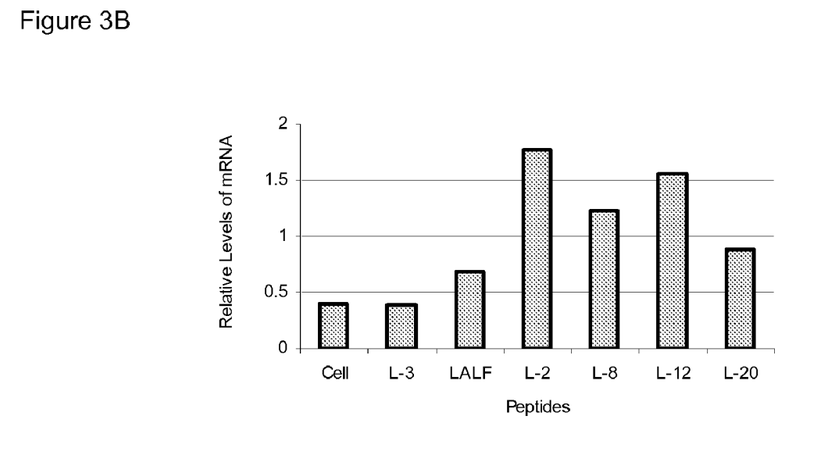

Effect of Analogous Peptides L-2, L-8, L-12 and L-20 on the Expression of IFN-α, IFN-γ and IL-12 in Human Mononuclear Cells For this assay, human mononuclear cells were isolated by a Ficoll-Hypaque gradient from a leukocyte concentrate or "Buffy Coat" of a donor. Up to 5×10$^6$ were seeded in 24-well plates in RPMI 1640 medium supplemented with 10% calf fetal serum. Each peptide was further added at 40 μg/ml in a 0.1 ml volume of RPMI medium and cells were cultured for 18 h at 37° C. and 5% of CO$_2$. Total RNA was extracted by using the TriReagent method. Afterwards, the expressions of IFN-α, IFN-γ and IL-12 genes were determined by the reverse transcription reaction and PCR amplification (RT-PCR kit, Perkin Elmer). Results are shown as relative amounts of messenger RNA normalized against expression levels of the β-actin housekeeping gene. Results obtained in this assay demonstrated that peptides L-2, L-8, L-12 and L-20 described in this invention are capable of inducing the expression of the IFN-α, IFN-γ and IL-12 genes, as shown in FIG. 3A. The analogous peptides L-2, L8 and L-12 are particularly more effective at inducing the expression of the IFN-α gene than the LALF$_{32-51}$ peptide, as shown in the FIG. 3B. This example demonstrates that aminoacid substitutions in the original LALF$_{32-51}$ sequence eliminate the capacity to bind LPS, subsequently enhancing the immunomodulatory effect of the resulting peptide.

Example 5

Figure 4A:
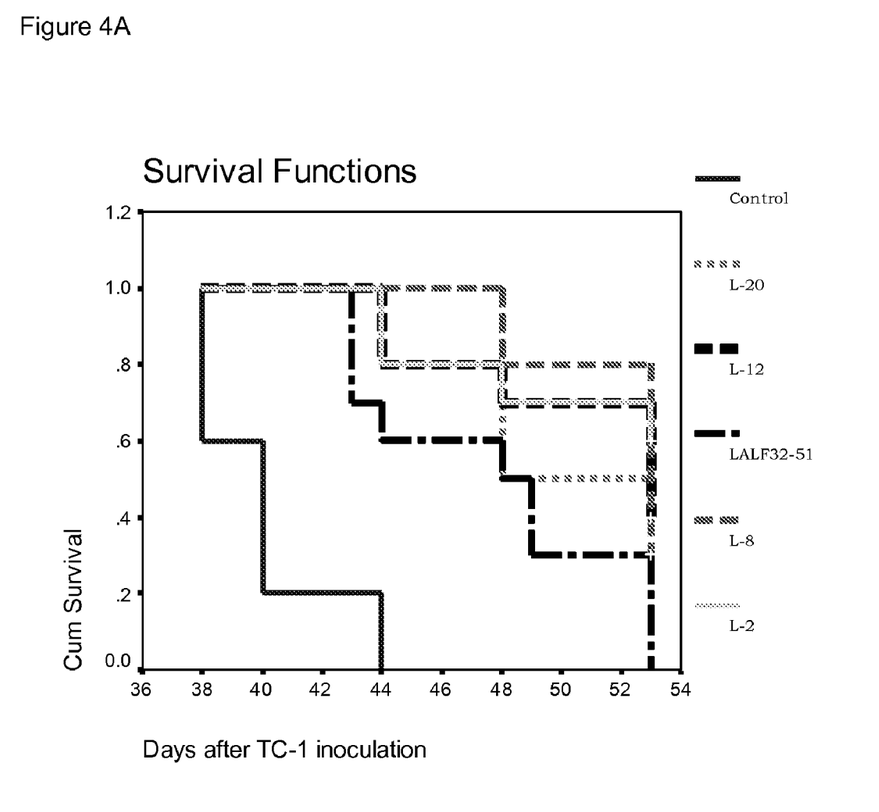
FIGS. 4a and 4b: Anti-tumoral effect of peptides in the TC-1 tumor model.
Figure 4B:
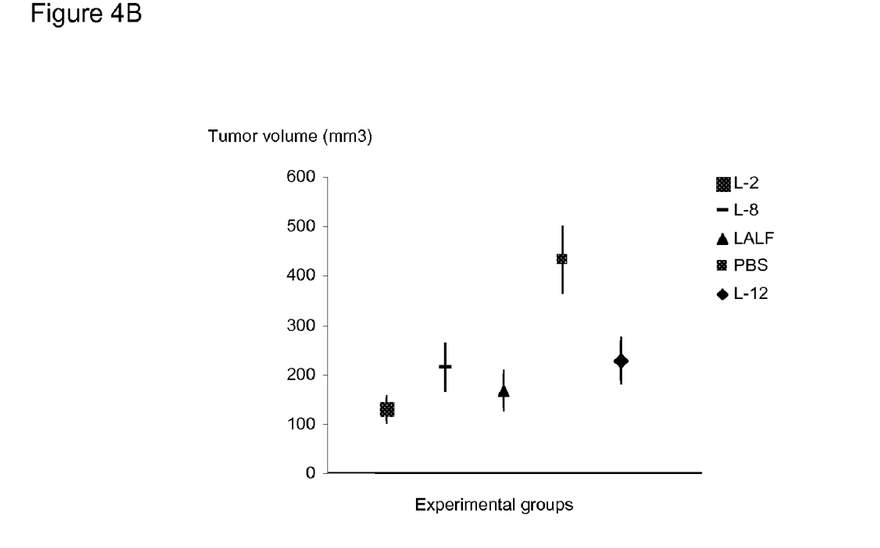

Anti-Tumoral Effect of Analogous Peptides L-2, L-8, L-12 and L-20 in the TC-1 Tumor Model Eight-to-ten weeks-old C57BI/6 female mice were used for this assay (n=10 animals per experimental group). For tumor graft, TC-1 tumor cells derived from C57BI/6 malignant epithelial lung cells were used, being resuspended in phosphate-buffered saline (PBS). An amount of 50,000 cells in a 200 μl volume was inoculated to mice by subcutaneous route in the right hind limb. The first peptide administration was carried out by subcutaneous route in the right flank once tumor reached a 100 mm$^3$ volume, and the second was carried out after 10 days. In this assay, a 4 mg per kg of weight dose was evaluated (80 μg/mice). Animal survival and tumor mass were the parameters evaluated to measure the anti-tumoral effect peptides of interest, as shown in FIGS. 4A and 4B. The analogous peptides L-2, L-8, L-12 and L-20 were effective for inhibiting tumor progression and prolonging survival of mice, respectively. These results evidence the anti-tumoral efficacy of analogous peptides in a solid tumor model in mice. The Log Rank method was used as statistical analysis for detecting significant differences between groups. Results evidenced that the analogous peptides L-2, L-8, L-12 and L-20 significantly increase the survival of animals, compared to the LALF$_{32-51}$ peptide (*p<0.05). These results demonstrate that substitutions of aminoacids in the original 32-51 sequence of the LALF protein could significantly increase the anti-tumoral capacity of the peptide.

Example 6

Anti-Tumoral Effect of the Analogous Peptide L-2 in a Melanoma Model

Figure 5A:
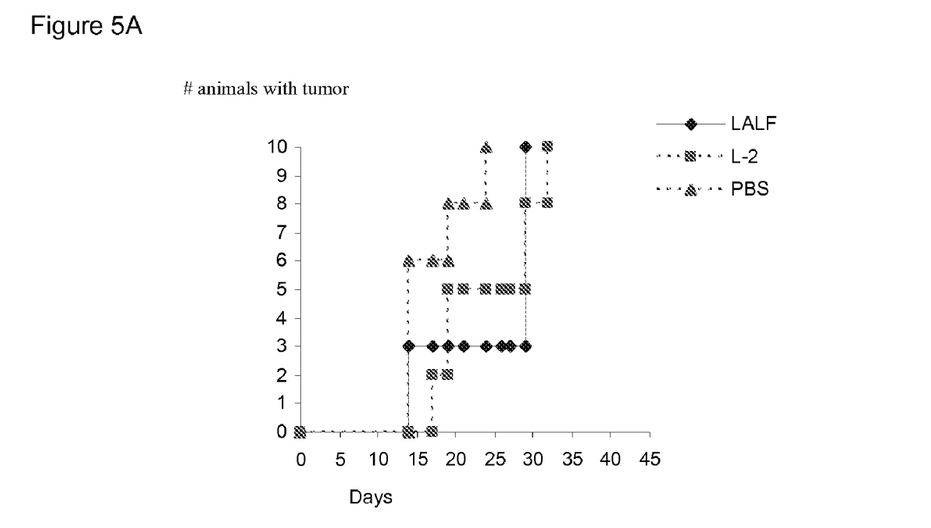
FIGS. 5a and 5b: Anti-tumoral effect of the L-2 peptide in the melanoma model.
Figure 5B:
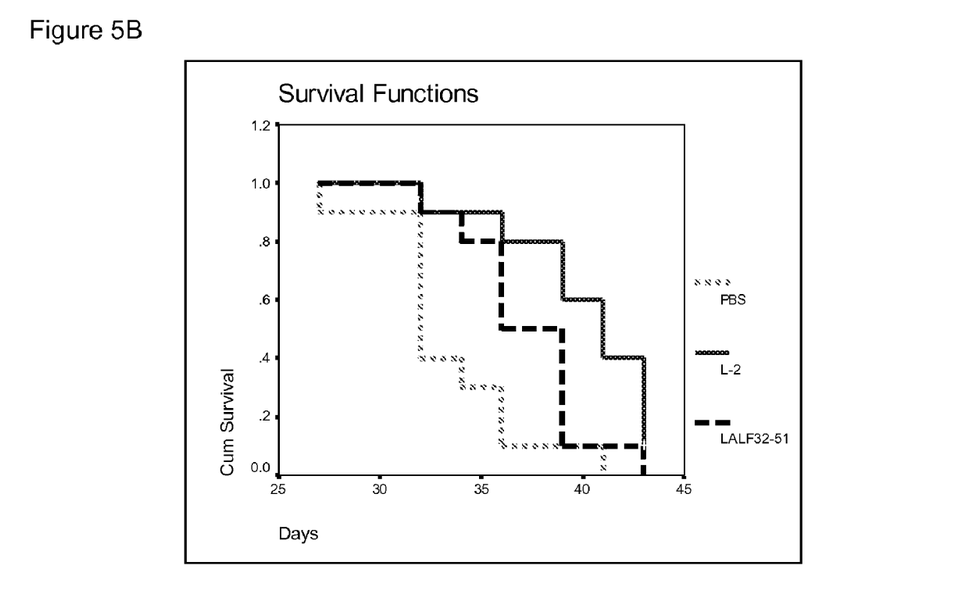

Eight-to-ten weeks-old C57Bl/6 female mice were used for this assay (n=10 animals per experimental group). For tumor graft, MB16-F10 tumor cells were used, being resuspended in phosphate-buffered saline (PBS). An amount of 15,000 cells were inoculated in a 200 µl volume by subcutaneous route in the right hind limb. After 4 days, the L-2 peptide was administered, with the second injection administered 7 after the first, and the third immunization was administered 14 days after. In this assay was evaluated a dose of 4 mg of peptide per kg of animal weight. Parameters evaluated to measure the anti-tumoral effect of the given peptide during this assay were the time of tumor grafting and the animal survival. As shown in FIG. 5A, the L-2 analogous peptide significantly delayed tumor grafting (*p<0.05, Log Rank method). The analysis of survival by the Log Rank method demonstrated that the L-2 peptide significantly increased the survival of animals (*p<0.05), being more effective than the LALF$_{32-51}$ peptide, as shown in FIG. 5B. These results evidence the anti-tumoral efficacy of the L-2 peptide not only against lung epithelial cancer cells, but also against cancer cells from other histological and anatomical parts of the body, like melanoma.

Example 7

Figure 6A:
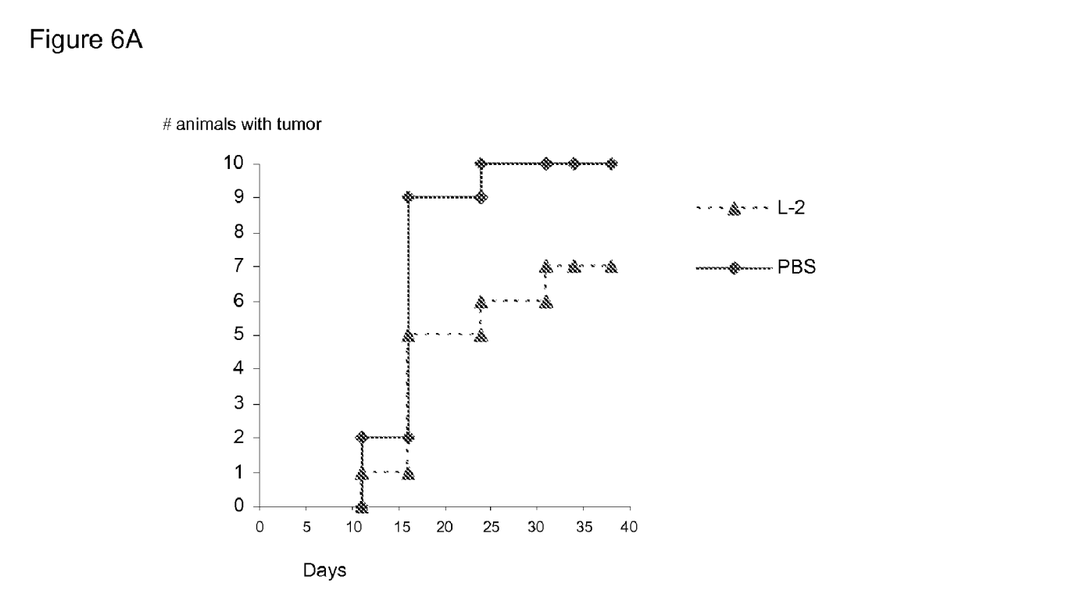
FIGS. 6a and 6b: Anti-tumoral effect of the analogous L-2 peptide in a prophylactic administration schedule of the TC-1 tumor model.
Figure 6B:
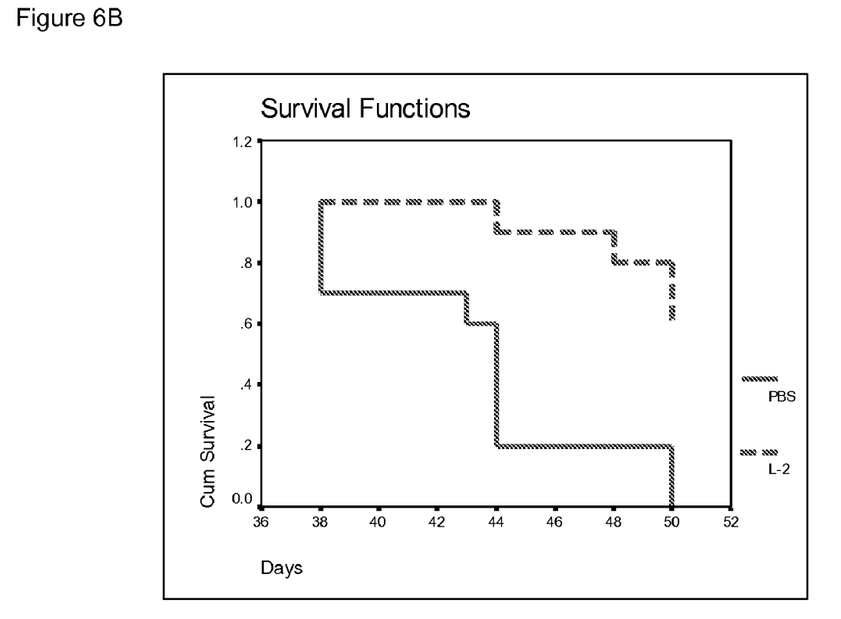

Anti-Tumoral Effect of the L-2 Analogous Peptide in a Prophylactic Schedule of Treatment, in the TC-1 Tumor Model Eight-to-ten weeks-old C57Bl/6 female mice were used for this assay (n=10 animals per experimental group). For tumor graft, TC-1 tumor cells, being resuspended in phosphate-buffered saline (PBS). Mice were first injected with the L-2 peptide (4 mg of peptide/kg of body weight). After 7 days, they received a second injection of the same dose; after 14 days of the first peptide injection, animals were inoculated with 50,000 cells in a 200 µl volume by subcutaneous route in the right hind limb. Parameters evaluated for measuring the anti-tumoral effect of the peptide included the time for tumor grafting (FIG. 6A) and the survival of animals (FIG. 6B). Results obtained in this assay demonstrated that the L-2 peptide of this invention was effective to prevent the development of the tumor and also increased the survival of the animals. These results evidence that the peptide of the present invention shows a prophylactic effect that prevents the establishment of the tumor.

Example 8

Figure 7A:
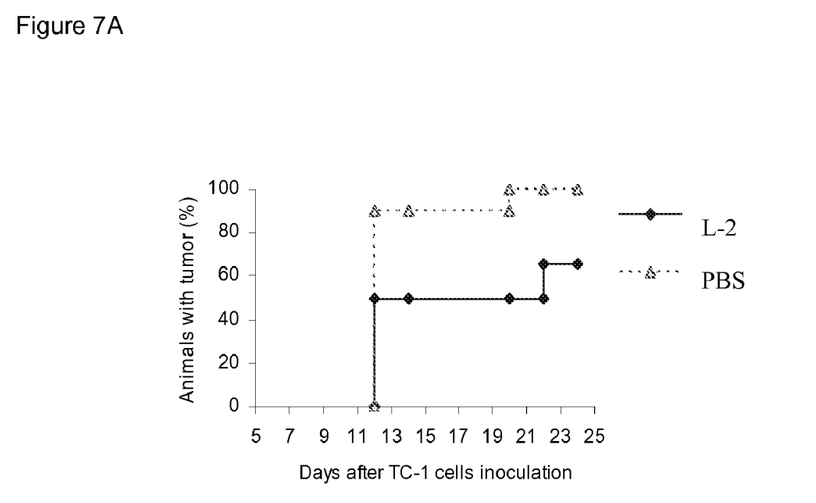
FIGS. 7a and 7b: Anti-tumoral effect of the analogous L-2 peptide in a double challenge schedule with TC-1 tumor cells.
Figure 7B:
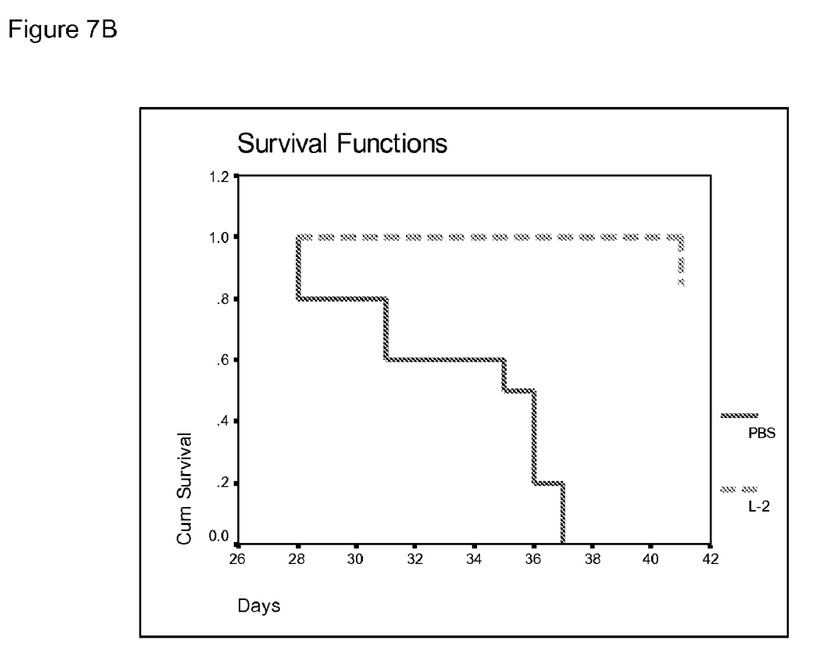

Anti-Tumoral Effect of the L-2 Analogous Peptide in a Double Challenge Schedule Animals without established tumors in the schedule of the previous example (n=6) were further challenged for a second time with 50,000 TC-1 cells in a 200 µl volume in PBS by subcutaneous route in the left hind limb (day 49 after the first challenge). The same amount of tumor cells were inoculated to "naïve" mice from the same litter as control group of the experiment, to guarantee the homogeneity in age, and were kept under the same conditions without receiving the peptide (n=10 animals). Parameters evaluated to measure the anti-tumoral effect of the L-2 peptide included the time of tumor grafting and animal survival. Results obtained in this assay demonstrate that the L-2 peptide is able to protect mice from a second challenge with tumor cells, retarding the establishment of the tumor (FIG. 7A) and increasing animal survival (FIG. 7B). This result evidences that the peptide of the invention is able to induce a sustained anti-tumoral response, still functional against a second challenge with tumor cells, evidencing the development of an antigen-specific adaptive immune response.

Example 9

Figure 8:
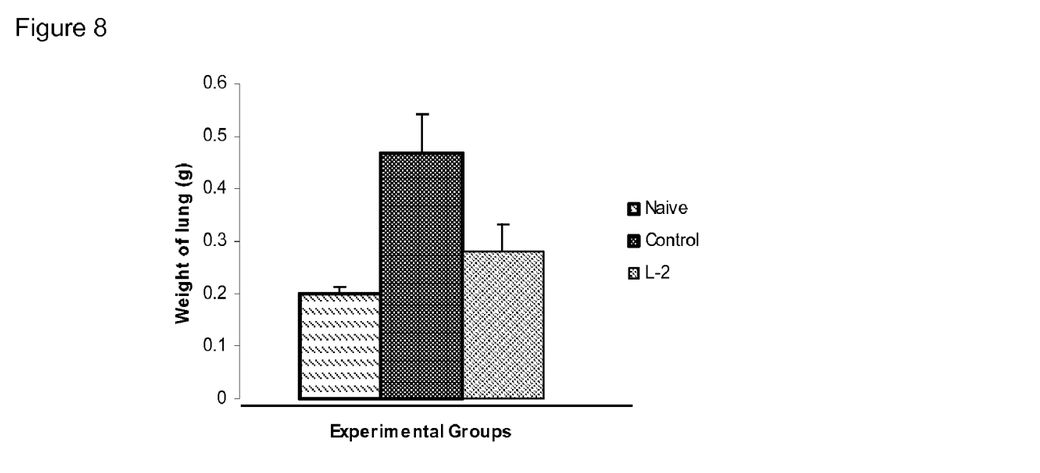
FIG. 8: Anti-metastatic capacity of the analogous peptide L-2.

Anti-Tumoral Effect of the L-2 Analogous Peptide in the Metastasis Model of Lewis' Carcinoma Eight-to-ten weeks-old C57Bl/6 female mice were used for this assay (n=8 animals per experimental group). These animals were inoculated in the posterior right footpad with 250,000 mice lung cancer 3LLD122 cells. After 7 days, a 4 mg/kg of body weight dose of the L-2 analogous peptide was subcutaneously injected. When tumors reached 8 mm in diameter, the primary tumor was surgically removed from the carrier leg. Mice were sacrificed 21 days after this surgical procedure. Lungs were weighed to indicate the amount of metastasis on them. The results shown in FIG. 8 indicate that the L-2 analogous peptide of this invention is able to reduce the metastatic tumor events.

Example 10

Effect of the L-2 Analogous Peptide on the Growth of Tumor Cells

Figure 9:
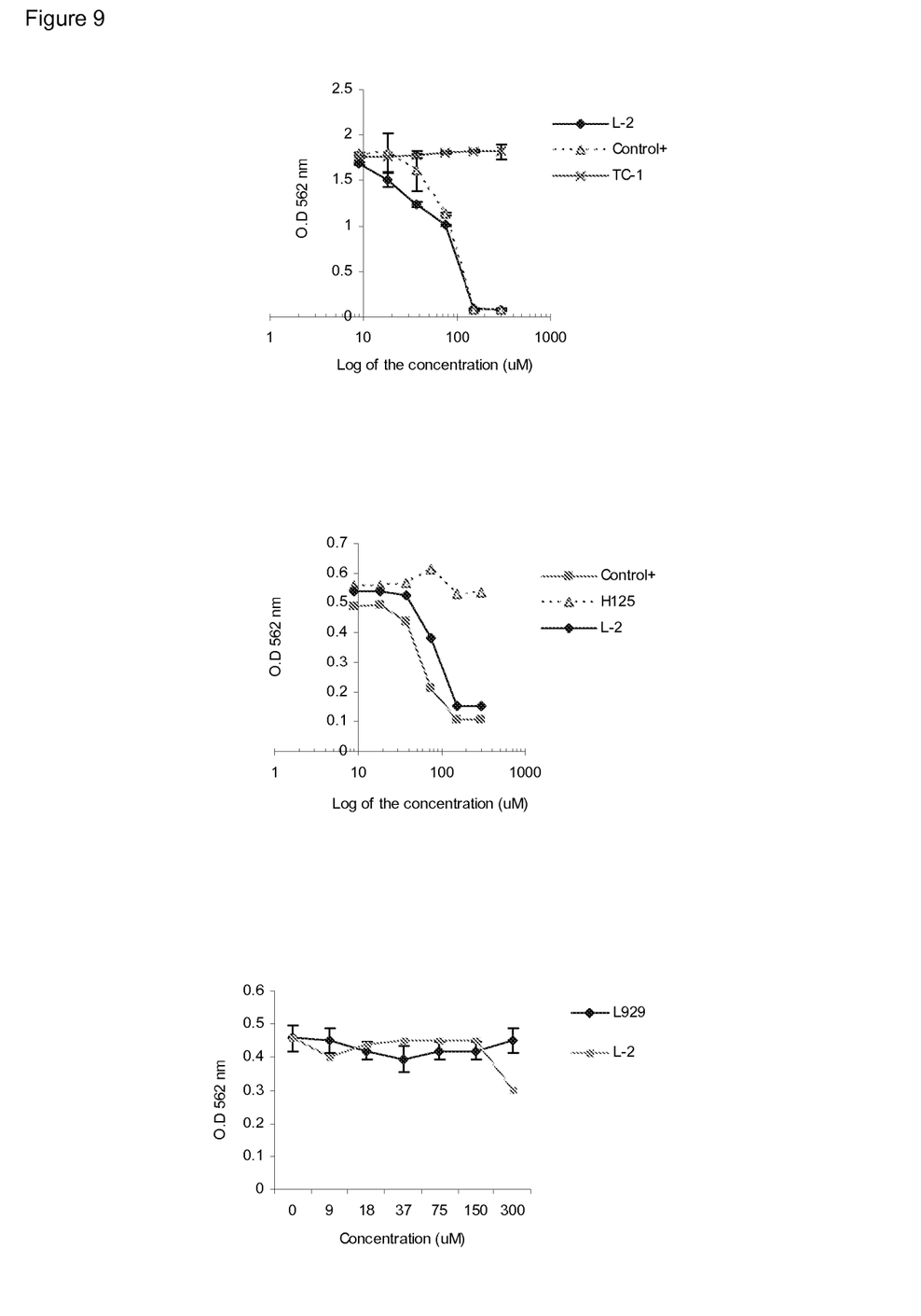
FIG. 9: Effect of the analogous peptide L-2 on the proliferation of TC-1, H125 and L929 cells.

For this assay, TC-1, H-125 (non-small human ling cancer cells) and L929) murine fibroblast) cells were seeded in 96-well culture plates (Costar) at a $2 \times 10^4$ cells/ml in Dulbecco's modified Eagle's medium (DMEM)(Gibco) supplemented with Calf Fetal Serum (Gibco). After 24 h, the peptides were added to the culture in a range of 9 µM to 300 µM. Plates were incubated for 72 h with 5% $CO_2$ and after that time, the assay was revealed with crystal violet. Plates were extensively washed with tap water and plates were read at 562 nm. Results are shown in FIG. 9. A pro-apoptotic peptide with a marked anti-proliferative effect in vitro was employed as positive control (Perea, S., et al (2004) Antitumor Effect of a Novel Proapoptotic Peptide that Impairs the Phosphorylation by the Protein Kinase 2 *Cancer Research* 64: 7127-7129). The results obtained demonstrated that the L-2 peptide produces a dose-dependent anti-proliferative effect on TC-1 and H-125 cells. However, no effect was detected with the peptide of the present invention in the murine fibroblast L929 cell line. This result demonstrates that the peptide of the present invention shows selective cytotoxic effect on tumoral cells in vitro.

INCORPORATION OF SUBSTITUTE SEQUENCE LISTING

Incorporated herein by reference in its entirety is a Substitute Sequence Listing for the application. The Substitute Sequence Listing is disclosed on a computer-readable ASCII text file titled, "substitute sequence.txt", created on Jul. 8, 2010. The Sequence.txt file is 5 kb in size.

The invention claimed is:

1. A synthetic peptide comprising a peptide selected from the group consisting of SEQ ID NO: 1; SEQ ID NO: 2; SEQ ID NO: 3; and SEQ ID NO: 4.

2. A pharmaceutical composition comprising a synthetic peptide according to claim 1 and an excipient or pharmaceutically acceptable vehicle.

3. The pharmaceutical composition according to claim 2, further comprising an antigen.

4. The pharmaceutical composition according to claim 3, wherein said antigen comprises a cancer antigen.

5. A synthetic peptide consisting of a peptide selected from the group consisting of SEQ ID NO: 1; SEQ ID NO: 2; SEQ ID NO: 3; and SEQ ID NO: 4.

6. A pharmaceutical composition comprising a synthetic peptide according to claim 5 and an excipient or pharmaceutically acceptable vehicle.

7. The pharmaceutical composition according to claim 6, further comprising an antigen.

8. The pharmaceutical composition according to claim 7, wherein said antigen comprises a cancer antigen.

9. A method for treating cancer comprising administering an effective amount of a synthetic peptide comprising a peptide selected from the group consisting of SEQ ID NO: 1; SEQ ID NO: 2; SEQ ID NO: 3, and SEQ ID NO: 4 to an animal or a human.

10. The method of claim 9, wherein said synthetic peptide is administered to a human.

11. The method of claim 10, wherein said human is immunosuppressed.

12. The method of claim 9, wherein metastasis is inhibited.

13. The method of claim 9, wherein tumor progression is inhibited.

14. A method for treating cancer comprising administering an effective amount of a synthetic peptide consisting of a peptide selected from the group consisting of SEQ ID NO: 1; SEQ ID NO: 2; SEQ ID NO: 3, and SEQ ID NO: 4 to an animal or a human.

15. The method of claim 14, wherein said synthetic peptide is administered to a human.

16. The method of claim 15, wherein said human is immunosuppressed.

17. The method of claim 14, wherein metastasis is inhibited.

18. The method of claim 14, wherein tumor progression is inhibited.

* * * * *

SEQUENCE LISTING

<160> NUMBER OF SEQ ID NOS: 13

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

His Ala Arg Ile Lys Pro Thr Phe Arg Arg Leu Lys Trp Lys Tyr Lys
1               5                   10                  15

Gly Lys Phe Trp
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

His Tyr Arg Ile Lys Pro Thr Ala Arg Arg Leu Lys Trp Lys Tyr Lys
1               5                   10                  15

Gly Lys Phe Trp
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

His Tyr Arg Ile Lys Pro Thr Phe Arg Arg Leu Ala Trp Lys Tyr Lys
1               5                   10                  15

Gly Lys Phe Trp
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

His Tyr Arg Ile Lys Pro Thr Phe Arg Arg Leu Lys Trp Lys Tyr Lys
1               5                   10                  15

Gly Lys Phe Ala
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

His Tyr Ala Ile Lys Pro Thr Phe Arg Arg Leu Lys Trp Lys Tyr Lys
1               5                   10                  15

Gly Lys Phe Trp
        20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

His Tyr Arg Ile Lys Pro Thr Phe Ala Arg Leu Lys Trp Lys Tyr Lys
1               5                   10                  15

Gly Lys Phe Trp
        20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

His Tyr Arg Ile Lys Pro Thr Phe Arg Arg Leu Lys Trp Lys Tyr Lys
1               5                   10                  15

Gly Lys Ala Trp
        20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

His Tyr Arg Ile Lys Pro Thr Ala Arg Arg Leu Ala Trp Lys Tyr Lys
1               5                   10                  15

Gly Lys Phe Trp
        20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

His Ala Arg Ile Lys Pro Thr Ala Arg Arg Leu Lys Trp Lys Tyr Lys
1               5                   10                  15

Gly Lys Phe Trp
        20

<210> SEQ ID NO 10
<211> LENGTH: 20
<212> TYPE: PRT

```
<213> ORGANISM: Artificial Sequence
<220> FEATURE:
<223> OTHER INFORMATION: Synthetic peptide

<400> SEQUENCE: 10

His Ala Arg Ile Lys Pro Thr Phe Arg Arg Leu Ala Trp Lys Tyr Lys
1               5                   10                  15

Gly Lys Phe Trp
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

His Ala Arg Ile Lys Pro Thr Ala Arg Arg Leu Ala Trp Lys Tyr Lys
1               5                   10                  15

Gly Lys Phe Trp
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

His Ala Arg Ile Lys Pro Thr Ala Arg Arg Leu Ala Trp Lys Tyr Lys
1               5                   10                  15

Gly Lys Phe Ala
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

His Tyr Arg Ile Lys Pro Thr Phe Arg Arg Leu Lys Trp Lys Tyr
1               5                   10                  15

Lys Gly Lys Phe Trp
            20
```